United States Patent [19]
Peglion et al.

[11] Patent Number: 5,945,566
[45] Date of Patent: Aug. 31, 1999

[54] AMINO COMPOUNDS OF 6,7,8,9-TETRAHYDRO-CYCLOPENTA[A]NAPHTHALENE AND OF 2,3-DIHYDRO-CYCLOPENTA[E]INDENE

[75] Inventors: Jean-Louis Peglion, Le Vesinet; Mark Millan, Le Pecq, both of France

[73] Assignee: Adir et Compagnie, Courbevoie, France

[21] Appl. No.: 09/166,951

[22] Filed: Apr. 9, 1998

[30] Foreign Application Priority Data

Apr. 10, 1997 [FR] France ................................. 97.04421

[51] Int. Cl.⁶ .................. C07C 213/00; C07C 233/00
[52] U.S. Cl. .................. 564/339; 564/306; 564/427; 564/163; 514/619; 514/621; 514/646; 514/656
[58] Field of Search ...................... 564/306, 339, 564/163, 427; 514/619, 621, 646, 656

[56] References Cited

FOREIGN PATENT DOCUMENTS 9860765 10/1998 Australia .
870759 10/1998 European Pat. Off. .

Primary Examiner—Paul J. Killos
Attorney, Agent, or Firm—The Firm of Gordon W. Hueschen

[57] ABSTRACT

New amino compounds of formula:

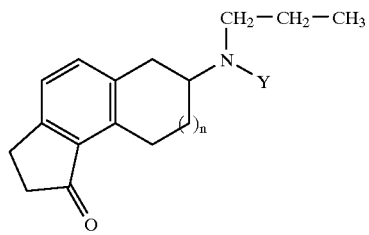

wherein n and Y are as defined in the description, in racemic form or in the form of optical isomers.

and addition salts thereof with pharmaceutically acceptable acids.

Those compounds may be used as medicaments.

6 Claims, No Drawings

AMINO COMPOUNDS OF 6,7,8,9-TETRAHYDRO-CYCLOPENTA[A] NAPHTHALENE AND OF 2,3-DIHYDRO-CYCLOPENTA[E]INDENE

The present invention relates to new amino compounds of 6,7,8,9-tetrahydro-cyclopenta-[a]naphthalene and of 2,3-dihydro-cyclopenta[e]indene, to a process for their preparation and to pharmaceutical compositions containing them.

It relates more especially to compounds of formula I:

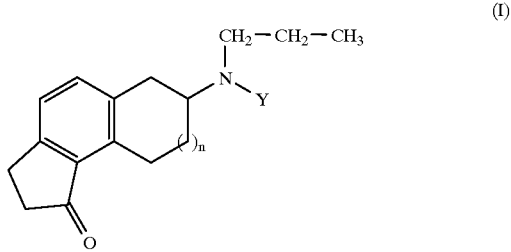

wherein
n represents zero or one; and
Y represents a hydrogen atom or a radical selected from those corresponding to formulae:

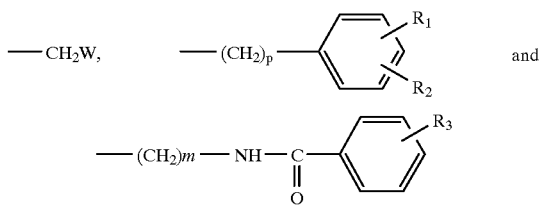

wherein
W represents a hydrogen atom or a straight-chain or branched alkyl, alkenyl or alkynyl radical each having from 1 to 5 carbon atoms,
p represents an integer from 1 to 5 inclusively,
$R_1$ and $R_2$, which may be the same or different, each represent a hydrogen or halogen atom or a hydroxy, $(C_1-C_5)$alkoxy, —NH—SO$_2$—CH$_3$, —NH—SO$_2$—CF$_3$, —NH—CO—CH$_3$, —NH—CO—CF$_3$ or

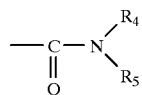

radical wherein $R_4$ and $R_5$, which may be the same or different, each represent a hydrogen atom or a straight-chain or branched $(C_1-C_6)$alkyl radical:
m represents an integer from 2 to 5 inclusively, and
$R_3$ represents a hydrogen or halogen atom or a hydroxy, $(C_1-C_6)$alkoxy, trifluoromethyl, cyano or phenyl radical;
in racemic form or in the form of optical isomers, and addition salts thereof with a pharmaceutically acceptable acid.

The compounds of formula I act as powerful dopaminergic ligands both in vitro and in vivo. Of the five known sub-types, $D_1$ to $D_5$, of dopaminergic receptors, the compounds of the present invention are more specific for the $D_3$ dopaminergic receptor sub-type.

Currently, the substances used therapeutically in the treatment of disorders in which the dopaminergic system is implicated all bind very strongly to the $D_2$ receptor sub-type, whether they are dopaminergic blockers (used in disorders that are attributable to hyperactivity of that neurotransmitter, such as, for example, in schizophrenia and psychotic disorders) or dopaminergic activators (used in disorders that are attributable to hypoactivity of that neurotransmitter, such as, for example, in Parkinson's disease). Those $D_2$ dopaminergic blockers or activators have, however, a number of side-effects: tardive dyskinesia, hyperprolactinaemia, amenorrhea in the case of the blockers, and cardiovascular and motor effects in the case of the activators.

$D_3$ receptors, the concentrations of which are very high in the limbic system but, unlike $D_2$ receptors, very low in the nigrostriated nucleus and in the lactotrophic cells, thus constitute a privileged site of action for molecules that act at the level of the dopaminergic system. Molecules that act preferentially on the $D_3$ dopaminergic, receptors, as is the case with the compounds of the present invention, therefore do not have the side-effects typically associated with $D_2$ receptor ligands, as mentioned above.

In fact, studies carried out in vitro (binding to cloned human dopaminergic receptors) with the compounds of the present invention show that they behave like ligands that have a high affinity for $D_3$ dopaminergic receptors.

That specificity of action makes the compounds of the present invention especially valuable for use as medicaments that act at the level of the dopaminergic system, especially in Parikinison's disease (*J. Neur. Transm.*, 1993, 94, 11–19), memory disorders (*Nature*, 1990, 347, 146–151), drug abuse (*Science*, 1993, 260, 1814), depression, schizophrenia and psychoses.

The present invention relates also to pharmaceutical compositions that comprise as active ingredient a compound of formula I or a physiologically tolerable salt thereof mixed or in association with one or more suitable pharmaceutical excipients.

The pharmaceutical compositions so obtained are generally presented in dosage form containing from 0.5 to 25 mg of active ingredient. For example, they may be in the form of tablets, dragées, gelatin capsules, suppositories or injectable or drinkable solutions, and may be administered orally, rectally or parenterally depending on the forms used.

The dosage varies according to the age and weight of the patient, the route of administration and associated treatments and ranges from 0.5 to 25 mg of active ingredient from one to three times per day.

The present invention relates also to a process for the preparation of the racemic or optically active compounds of formula I, characterised in that
a tertiary amine of formula II:

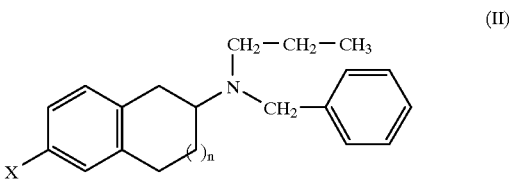

wherein X is a halogen atom selected from the atoms bromine and iodine and n is as defined above,
is reacted with butyllithium and dimethylformamide in tetrahydrofuran to obtain an aldhehyde of formula III:

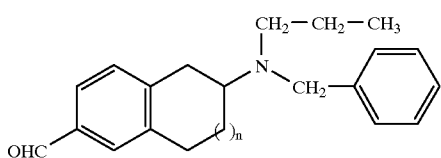

wherein n is as defined above, which is treated with malonic acid in pyridine in the presence of piperidine to yield a compound of formula IV:

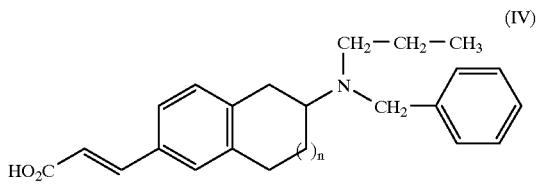

wherein n is as defined above, which is hydrogenated in the presence of palladium-on-carbon to yield an acid of formula formula V:

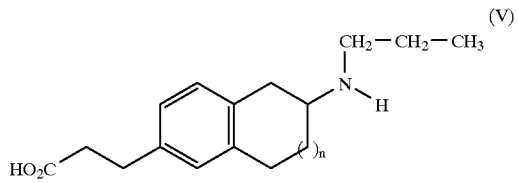

wherein n is as defined above, which is cyclised using hot polyphosphoric acid to yield a compound of formula I':

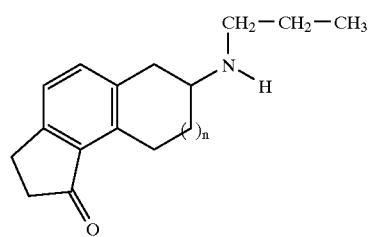

wherein n is as defined above, which is treated with a compound of formula VI:

wherein Hal is a halogen atom selected from the atoms chlorine, bromine and iodine, and $Y_1$ has the meanings of Y, except for the meaning hydrogen, to yield a compound of formula I":

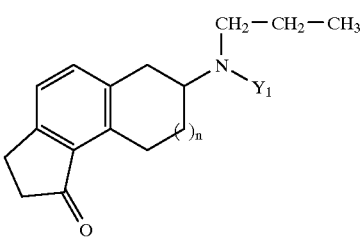

wherein n is as defined above and $Y_1$ has the meanings of Y except for the meaning hydrogen.

The totality of the compounds I' and II" constitutes the totality of the compounds of formula I.

If desired, starting from the racemic mixtures, the optical isomers are prepared in accordance with conventional methods of the literature.

The salts of the compounds of formula I with pharmaceutically acceptable acids are obtained in accordance with conventional methods, as indicated in the Examples below. The starting materials are either known products or products that are obtained starting from known substances in accordance with methods known from the literature.

The following Examples, which are non-limiting, illustrate the present invention. The melting points are determined using a Kofler hot plate under a microscope.

EXAMPLE 1

(7R,S)-7-(N-Propylamino)-6,7,8,9-tetrahydro-cyclopenta[a]naphthalen-1-one and the Hydrochloride Thereof Step 1: (7R,S)-3-Formyl-7-(N-benzyl-N-propylamino)-5,6,7,8-tetrahydronaphthalene 19.5 g (0.0544 mol) of (7R,S)-3-bromo-7-(N-benzyl-N-propylamino)-5,6,7,8-tetrahydronaphthalene are dissolved in 0.243 liter of tetrahydrofuran and cooled to −65° C. At that temperature, 51 ml of a 1.6M butyllithium solution in tetrahydrofuran are poured in. After the pouring is complete, the mixture is left for 2 hours and then, still at that temperature, a solution of 12.3 ml of dimethylformamide in 28 ml of tetrahydrofuran is added. After one hour at −65° C. the mixture is left at room temperature over a weekend. The mixture is taken up in water and ether and decanting is carried out, followed by drying and evaporation to obtain 16.3 g of an oil that corresponds to the expected product. (Yield=93%)

Step 2: 3-[(7R,S)-7-(N-Benzyl-N-propylamino)-5,6,7,8-tetrahydronaphthalen-3-yl]-propenoic acid 6.9 g (0.022 mol) of the compound obtained in the preceding step, 11.3 g (0.045 mol) of malonic acid, 2.22 ml (0.022 mol) of piperidine and 82.7 ml of pyridine are heated at 90° C. for three hours and then at reflux for 2 hours. The mixture is left overnight at room temperature, concentrated and taken up in N-hydrochloric acid and methylene chloride. Decanting is carried out, followed by drying over $MgSO_4$ and evaporation to yield 8 g of crystals that melt at 196° C. and correspond to the expected product.

Step 3: 3-[(7R,S)-7-(N-Propylamino)-5,6,7,8-tetrahydronaphthalen-3-yl]-propionic acid 0.8 g of the compound obtained in the preceding step, 1 g of ammonium formate, 0.3 g of 10% Pd/C and 25 ml of methanol are refluxed for 4 hours. After filtration, the reaction mixture is concentrated to obtain 0.4 g of a pink solid that melts at 155° C. and corresponds to the expected product. (Yield=74%)

Step 4: Title compound 3 g of the compound obtained in the preceding step are added all together to 30 ml of polyphosphoric acid that has already been heated to 75° C. The temperature then rises to 92° C. The mixture is maintained at that temperature for one hour. Heating is stopped and the temperature is allowed to fall to 45° C., and the mixture is then poured into ice. The mixture is rendered basic with concentrated sodium hydroxide solution and extracted with ethyl acetate. Drying and evaporation yield 1.4 g of an oil which is purified by HPLC using a Nucleoprep 100-20 column, the mobile phase being made up of a $CH_2Cl_2/C_2H_5OH/CF_3CO_2H$ mixture in a ratio of 100/5/1. 0.73 g of the expected product is obtained (yield=26.6%) which is converted into the hydrochloride with ethereal hydrogen chloride. M.p. of the expected hydrochloride: 260–264 ° C.

EXAMPLE 2

(7R,S)-7-(N,N-Dipropylamino)-6,7,8,9-tetrahydro-cyclopenta[a]-naphthalen-1-one and the Hydrochloride Thereof 141 mg (0.58 mmol) of the title compound of Example 1 are dissolved in 8.4 ml of acetonitrile. 0.41 g (3 mmol) of anhydrous $K_2CO_3$ and 0.3 ml (3 mmol) of propyl iodide are then added. The mixture is stirred at room temperature for 48 hours. The solvent is removed by evaporation and the residue is taken up in 1N sodium hydroxide and ethyl acetate. The organic phase is washed until neutral, dried over $MgSO_4$ and then evaporated to yield the expected product, which is treated with ethereal hydrogen chloride to yield 40 mg of the hydrochloride. M.p.>260° C. (yield=21.5%).

EXAMPLE 3

(7R,S)-7-{N-Propyl-N-[4-(o-trifluoromethylbenzamido)butyl]amino}-6,7,8,9-tetrahydro-cyclopenta[a]naphthalen-1-one and the Hydrochloride Thereof 2 g (15 mmol) of anhydrous $K_2CO_3$ and 1.11 g (3.5 mmol) of N-(4-bromobutyl)-o-trifluoromethylbenzamide are added to a solution of 0.7 g (2.9 mmol) of the title compound o)f Example 1 in 50 ml of methyl isobutyl ketone. The mixture is heated at 75° C. for 12 hours and then, after cooling, the solvent is removed by evaporation and the residue is taken up in water and methylene chloride. Decanting is carried out, followed by drying over $MgSO_4$ and evaporation to obtain an oil, which is treated with ethereal hydrogen chloride to yield 0.68 g of the hydrochloride of the expected product.

By proceeding in the same manner as in Example 3, the compounds of the following Examples were obtained:

EXAMPLE 4

(7R,S)-7-{N-Propyl-N-[4-(o-fluorobenzamido)butyl]amino}-6,7,8,9-tetrahydro-cyclopenta[a]naphthalen-1-one

EXAMPLE 5

(7R,S)-7-{N-Propyl-N-[3-(o-methoxybenzamido)propyl]amino}-6,7,8,9-tetrahydro-cyclopenta[a]naphthalen-1-one

EXAMPLE 6

(7R,S)-7-{N-Propyl-N-[3-(o-bromobenzamido)propyl]amino}-6,7,8,9-tetrahydro-cyclopenta[a]naphthalen-1-one

EXAMPLE 7

Pharmacological Study

The selectivity for $D_3$ receptors compared with that for $D_2$ receptors was demonstrated:

in vitro: by the $D_2$ and $D_3$ receptor binding technique.

in vivo: by the capacity of the compounds of the invention to modulate hypothermia induced in the rat by the $D_3$ dopaminergic agonist: 7-OH-DPAT, (cf.: M. J. Millan et al. *J. Pharmacol. Exp. Ther.*, 1995, 275, 885).

✓ In vitro: human $D_2$ and $D_3$ receptor binding study

Cell culture

CHO (Chinese Hamster Ovary) cells were transfected in a stable manner by the gene that codes for the human dopamine $D_2$ or $D_3$ receptor according to methods known from the literature. The native cells are deficient in the enzyme DHFR (DiHydroFolate Reductase). The cells are cultured in an incubator at 37° C. in a humid atmosphere of 5% $CO_2$/95% air. The transfections are carried out using Lipofectin (Gibco). The CHO cells, co-transfected with the human $D_2$ receptor and the gene for resistance to phleomycin, were selected for their resistance to the presence of that antibiotic in the culture medium. The cells transfected with the human $D_3$ receptor were selected in a medium containing no hypoxanthine/thymidine in the presence of methotrexate. The compositions of the culture media used are: for CHO-$D_2$: DMEM (Dulbecco's Modified Eagle Medium) supplemented with 10% foetal calf serum and hypoxanthine/thymidine; and for CHO-$D_3$: DMEM supplemented with 10% dialysed foetal calf serum. The cells are harvested at confluence and the membranes are then prepared.

Membrane preparation

After a few minutes in the presence of 0.2% trypsin, the cells are recovered and centrifuged at 2000 g for 5 minutes. The cell mass, which is resuspended in 10 mM Tris-HCl buffer.

pH 7.5, containing 5 mM $MgSO_4$, is then passed over Polytron®. The homogenate is then centrifuged at 50000 g for 15 minutes, and the mass is resuspended by gentle sonication in an incubation buffer of the following composition: 50 mM Tris-HCl, pH 7.5 containing 120 mM NaCl, 5 mM KCl, 2 mM $CaCl_2$, 5 mM $MgCl_2$. The membranes are then divided into aliquots and stored at −80° C. until the experiment day.

Binding experiments

Incubation is carried out in polypropylene tubes at a final volume of 400 μl containing:

100 μl of [$^{125}$I]-iodosulpride (Amersham) at 0.1 and 0.2 nM for the $D_2$ and $D_3$ receptors, respectively.

100 μl of buffer (total tubes)

or 100 μl of 10 μM raclopride (non-specific binding)

or 100 μl of compound

200 μl of membrane preparation containing the $D_2$ or $D_3$ receptors in a buffer to which 0.2% BSA (bovine serum albumin) has been added.

The ranges of concentration of each compound include at least seven points determined in triplicate, each experiment being repeated at least twice.

The incubation, which lasts for thirty minutes at 30° C., is terminated by means of rapid filtration over a Brandle apparatus, followed by three consecutive rinses with Tris-HCl buffer, pH 7.4, containing 120 mM NaCl. The filters recovered are then counted using a gamma counter.

Analysis of the results

The $IC_{50}$, which represents the concentration that gives 50% inhibition of the radioligand binding, is calculated by non-linear regression (Prism Graph method).

The $K_i$ value is derived from the formula $K_i=IC_{50}/(1+L/Kd)$ where L is the concentration of [$^{125}$I]-iodosulpride used in the experiment and Kd is its dissociation constant. The results are expressed in the form of $pK_i$ ($pK_i=-logK_i$).

For human $D_2$ and $D_3$ receptors, the Kd are, respectively, 0.5 and 1.31 nM.

✓ In vivo: hypothermia in the rat

The tests are carried out on male Wistar rats weighing 200–250 g which are placed in individual cages with free access to food and water. The compounds are solubilised in distilled water to which a few drops of lactic acid are added. The injections are administered subcutaneously in a volume of 1.0 ml/kg. The doses are expressed in terms of the base. The rectal temperature of the rats is taken using a digital thermistoprobe (Millan et al. *J.P.E.T.* 1993, 264, 1364–1376). Initially, the rats are injected with the test compound or with the carrier and are then returned to their cages for thirty minutes. The rats are then given an injection of 7-OH-DPAT (0.16 mg/kg) and are returned to their cages. Thirty minutes later, the rectal temperature is measured and the difference determined in comparison with the base values ($\Delta T°$ C.). The Inhibitory Dose (95% confidence limits) to reduce the effect of the 7-OH-DPAT by 50% is calculated using the Finney method (Statistical Method in Biological Assays. 2nd ed. Hafner publishing, New York, 1964).

✓ Results

The compounds of the invention have very good affinity for the $D_3$ receptor. By way of example, the compound of Example 2 has a $pK_i$ of 8.0.

Moreover, the compounds of the invention all demonstrate a selectivity which, compared with that for the $D_2$ receptor, is greater by a factor of 10.

We claim:

1. An amino compound selected from those of formula I:

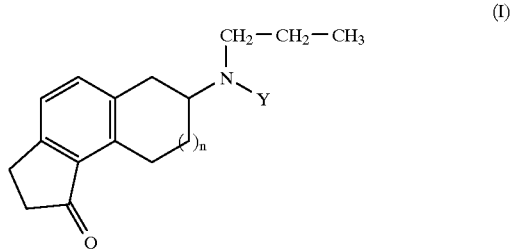

wherein n represents zero or one and

Y represents hydrogen or a group selected from those corresponding to formulae:

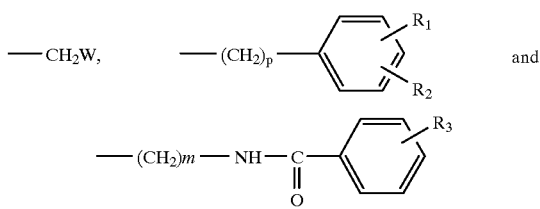

wherein:

W represents hydrogen or straight-chain or branched alkyl, alkenyl, or alkynyl, each having 1 to 5 carbon atoms inclusive, p represents 1 to 5 inclusive, $R_1$ and $R_2$, which may be the same, or different, each represent hydrogen, halogen, hydroxy, ($C_1$–$C_5$)alkoxy, —NH—$SO_2$—$CH_3$, —NH—$SO_2$—$CF_3$, —NH—CO—$CH_3$, —NH—CO—$CF_3$ or

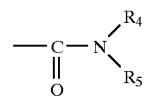

wherein $R_4$ and $R_5$, which may be the same or different, each represent hydrogen or straight-chain or branched ($C_1$–$C_6$) alkyl:

m represents 2 to 5 inclusive, and $R_3$ represents hydrogen, halogen, hydroxy, ($C_1$–$C_6$) alkoxy, trifluoromethyl, cyano or phenyl;

in racemic form or in the form of an optical isomer, and addition salts thereof with a pharmaceutically acceptable acid.

2. A compound of claim 1 selected from the group consisting of:

(7R,S)-7-(N-propylamino)-6,7,8,9-tetrahydro-cyclopenta[a] naphthalen-1-one and the hydrochloride thereof, (7R,S)-7-(N,N-dipropylamino)-6,7,8,9-tetrahydro-cyclopenta[a]naphthalen-1-one and the hydrochloride thereof, (7R,S)-7-{N-propyl-N-[4-(o-trifluoromethylbenzamido) butyl]amino}-6,7,8,9-tetrahydro-cyclopenta[a] naphthalen-1-one and the hydrochloride thereof, (7R,S )-7-{N-propyl-N-[4-(o-fluorobenzamido)butyl] amino}-6,7,8,9-tetrahydro-cyclopenta[a]naphthalen-1-one, (7R,S)-7-{N-propyl-N-[3-(o-methoxybenzamido)propyl] amino}-6,7,8,9-tetrahydro-cyclopenta[a]naphthalen-1-one, (7R,S)-7-{N-propyl-N-[3-(o-bromobenzamido)propyl] amino}-6,7,8,9-tetrahydro-cyclopenta[a]naphthalen-1-one.

3. A compound of claim 1 which is (7R,S)-7-(N,N-dipropylamino)-6,7,8,9-tetrahydro-cyclopenta[a] naphthalen-1-one or the hydrochloride thereof.

4. A compound of claim 1 which is (7R,S)-7-{N-propyl-N-[4-(o-trifluoromethylbenzamido)butyl]amino}-6,7,8,9-tetrahydro-cyclopenta[a]naphthalen-1-one or the hydrochloride thereof.

5. A method for treating a living animal body afflicted with a disease or disorder selected from Parkinson's disease, memory disorders, disorders associated with drug abuse, depression, schizophrenia, or psychoses, comprising the step of administering to the said living animal body an amount of a compound of claim 1 which is effective for alleviation of said disease or disorder.

6. A pharmaceutical composition, useful in treating a disease or disorder selected from Parkinson's disease, memory disorders, disorders associated with drug abuse, depression, schizophrenia, or psychoses, comprising as active ingredient a compound as claimed in claim 1 together with one or more pharmaceutically-acceptable excipients or vehicles.

* * * * *

UNITED STATES PATENT AND TRADEMARK OFFICE
CERTIFICATE OF CORRECTION

PATENT NO. : 5,945,566
DATED : Aug. 31, 1999
INVENTOR(S) : Jean Louis Peglion and Mark Millan It is certified that error appears in the above-indentified patent and that said Letters Patent is hereby corrected as shown below:

Column 2, line 31: "Parikinison's" should be
 -- Parkinson's --.

Column 7, line 51: Insert a -- comma -- before the word "and".

Column 8, line 17: Insert a -- comma -- before "or".

Column 8, line 19: Insert a -- hyphen -- between "pharmaceutically" and "acceptable".

Signed and Sealed this

Eighteenth Day of January, 2000

Attest:

Q. TODD DICKINSON

*Attesting Officer*  *Commissioner of Patents and Trademarks*